(12) United States Patent
Luxich et al.

(10) Patent No.: US 8,541,740 B2
(45) Date of Patent: Sep. 24, 2013

(54) DEVICE AND METHOD FOR ELECTRON BEAM ENERGY VERIFICATION

(75) Inventors: Penny Luxich, Stockton, NJ (US); Michael C. Saylor, Vienna, VA (US)

(73) Assignee: Ethicon, Inc., Somerville, NJ (US)

( * ) Notice: Subject to any disclaimer, the term of this patent is extended or adjusted under 35 U.S.C. 154(b) by 292 days.

(21) Appl. No.: 13/036,073

(22) Filed: Feb. 28, 2011

(65) Prior Publication Data

US 2012/0217390 A1    Aug. 30, 2012

(51) Int. Cl.
*G01J 1/00*    (2006.01)

(52) U.S. Cl.
USPC ................................................. 250/336.1

(58) Field of Classification Search
USPC ................................................. 250/336.1
See application file for complete search history.

(56) References Cited

U.S. PATENT DOCUMENTS

| | | | |
|---|---|---|---|
| 4,877,961 A | 10/1989 | McIntyre et al. | |
| 5,464,978 A | 11/1995 | Kudo et al. | |
| 6,225,622 B1 | 5/2001 | Navarro | |
| 6,364,529 B1 | 4/2002 | Dawson | |
| 6,429,444 B1 | 8/2002 | Korenev et al. | |
| 6,979,829 B2 | 12/2005 | Calvert et al. | |
| 7,580,504 B2 | 8/2009 | Lang et al. | |
| 7,780,352 B2 | 8/2010 | Fox et al. | |
| 2001/0004394 A1* | 6/2001 | Siffert et al. | 378/56 |
| 2002/0139939 A1* | 10/2002 | Takayama et al. | 250/492.3 |
| 2003/0098354 A1* | 5/2003 | Steklenski et al. | 235/487 |
| 2004/0228435 A1 | 11/2004 | Russell | |
| 2006/0027756 A1* | 2/2006 | Thomson et al. | 250/370.07 |

FOREIGN PATENT DOCUMENTS

WO    WO 00/39608    7/2000

OTHER PUBLICATIONS

Allen, et al., A Fully Integrated 10 MeV Electron Beam Sterilization System Radiat. Phys. Chem. vol. 46, No. 4-6 (1995) pp. 457-460.

An 11-Step, step wedge penetrometer made of aluminum used in quality assurance for medical xray applications' Oprax Medical Company. http://www.coneinstruments.com/step-wedge—penetometer/camid//cp/608111/.

DeSouza, C.N. et al "Evaluation of the depth-ratio and backscattering-factor methods in quality control measurements of electron beam energies" Applied Radiation and Isotopes vol. 63 (2005) pp. 217-222.

Duggan, L. et al, 'Investigation of dose reduction in neonatal radiography using specially designed phantoms and LiF:Mg,Cu,P TLDs' The British Journal of Radiology. vol. 76 (2003) pp. 232-237.

(Continued)

*Primary Examiner* — David Porta
*Assistant Examiner* — Hugh H Maupin
(74) *Attorney, Agent, or Firm* — David R. Crichton; Leo B. Kriksunov

(57) ABSTRACT

The present invention is directed to a device and system for verifying the electron beam kinetic energy spectrum and determining changes in kinetic electron beam energy spectrum that comprises a radiation-absorbing mass defined by a top surface, a bottom surface, and side walls, said mass having at least four separate slots containing one or more of dosimeter strips, wherein said slots are located at different depths within the mass as measured from the top surface of the mass, and said slots are positioned substantially parallel to the top surface of the mass. The present invention also relates to a method of determining and comparing changes in a kinetic electron energy spectrum.

13 Claims, 10 Drawing Sheets

(56) References Cited

OTHER PUBLICATIONS

Fuochi, P.G., et al, Evaluation test of the energy monitoring device in industrial electron beam facilities Radiation Physics and Chemistry vol. 78 (2009) pp. 481-484.

Kovacs et al., 'Dosimetry Procedures in Electron Processing' A.I.I.I. Newsletter, No. 25, vol. 1 & 2 (1992) pp. 242-251.

"Standard Practice for Dosimetry in an Electron Beam Facility for Radiation Processing at Energies Between 300 ke and 25 MeV." ISO/ASTM 51649. (2005).

Sturtewagen, E., et al., 'Multi-dimensional dosimetric verification of stereotactic radiotherapy for uveal melanoma using radiochromic EBT film' Z. Med. Phys. vol. 18 (2008) pp. 27-36.

\* cited by examiner

DEVICE AND METHOD FOR ELECTRON BEAM ENERGY VERIFICATION

FIELD OF THE INVENTION

The present invention is directed to a device, system and methods for verifying the electron beam kinetic energy spectrum and determining changes in kinetic electron beam energy spectrum, particularly for use in system for sterilizing healthcare products (e.g. medical devices, pharmaceuticals, combination products).

BACKGROUND OF THE INVENTION

Many products are irradiated using industrial irradiators such as electron beam (e-beam) sterilizers. Electron beam accelerators are used in a variety of applications such as pharmaceutical/medical device sterilization, food and cosmetic sanitization, industrial cross-linking and gem treatment. Industrial electron beam irradiators accelerate electrons through products such as pharmaceuticals, biologics, and medical devices as said products move in front of the radiation source (i.e. scan horn). The electron's kinetic energy is measured in electron volts. The radiation kinetic energy (electron volts), number of electrons accelerated and the time during which the product is exposed determines the amount of radiation, which is absorbed within the product.

The depth-dose profile within the product is directly tied to the kinetic energy spectrum. Not all parts of the product absorb the same amount of radiation since the energy accumulation can come from both direct (attenuation) and indirect (build-up) absorption of energy. Said absorption characteristics are heavily influenced by the kinetic energy of the accelerated electrons. Thus, the lowest level of radiation absorption within the depth-dose profile must be sufficient to sterilize (treat) the product while the highest radiation absorption within the depth-dose profile must not negatively impact the functionality of the product. This is especially important when the product includes biologic or active components that are sensitive to radiation absorption. Once a depth-dose profile is established for a given product, it is important to ensure that the profile does not vary beyond permissible limits.

Products may have components which are adversely affected by exposure to radiation above pre-determined levels (e.g., biologics) and variations in the radiation absorption applied to those products may greatly influence their functionality. Radiation absorption is a function of the radiation kinetic energy (e.g., electron-volts), number of electrons, movement in front of the radiation source, and the duration of application to the product at a specific depth within the product. Time (duration) is easy to measure. However, techniques known to directly measure electron kinetic-energy and related kinetic energy spectrum are labor intensive, expensive and have difficulty in diagnosing subtle changes in electron beam energy. These subtle changes may impact the depth dose profile of sensitive products (such as combination products and pharmaceuticals). Currently, technologies are not readily available to be utilized as a benchmark to diagnose changes in the electron beam energy. The current technologies available directly measure said energy.

The current mechanism for formal electron beam measurement is largely based on a human element to establish a tangent line based on the depth dose within the irradiation target or phantom. Subtle changes in the estimation of said tangent line can impact stated electron energy by a large margin. A device is necessary to verify and monitor electron beam energy, which is solely based on radiation physics, not a human interpretation of the data. Currently, automated systems are available to remove or reduce the human element, however, these systems are very expensive, take experience to utilize said systems, and are difficult to transport to an array of processing sites.

The current technology utilizes a very rough estimate of probable electron energy spectra and the design is built to measure said energy based on confluent layer(s) of dosimeter(s). Dosimeter placement is not tied to radiation physics but a confluent placement pattern to find the point in which energy is no longer deposited.

The current measurement of energy is performed very infrequently (monthly or quarterly) which can lead to process changes that could potentially impact the validated state of the process. A monitor, or comparator, design could be utilized during each and every processing event to ensure compliance to the original validation event ensuring the product's integrity.

There are numerous technologies available to measure the kinetic energy for electrons as per ISO/ASTM 51649, entitled "Standard Practice for Dosimetry in an Electron Beam Facility for Radiation Processing at Energies Between 300 keV and 25 MeV". The methodology in ISO/ASTM 51649 requires numerous dosimetry measurements or requires the use of specialized film reading equipment and substantial investment of time and highly specialized skills are required; therefore, this measurement is performed on a very sparse basis. U.S. Pat. No. 5,464,978 to Kudo et al. details an electron energy spectrometer having an electron energy analyzer equipped with plural detectors including a reference detector, with the spectrometer having a hemispherical electrostatic energy analyzer.

The published standard ISO/ASTM 51649 describes the procedure for performing an energy measurement for e-beam systems. The procedure includes instructions for placing the measurement device on a conveyor and describes moving a phantom across a radiation source. The definition of $R_{50}$ or half-value depth is defined as the depth in a homogeneous material at which the absorbed dose has decreased to 50% of its maximum value. The published standard ISO/ASTM 51649:2005 further describes two different types of energy measurement devices, referred to as a stack and a wedge. In conjunction with a film dosimetry system, the devices may be used to measure the depth dose distributions in a defined reference material. In addition to aluminum, low density materials such as polyethylene, polystyrene, graphite, polymethylmethacrylate (PMMA), and nylon may be used for the reference material. However, this methodology details how to calculate kinetic energy.

An article entitled "Investigation of dose reduction in neonatal radiography using specially designed phantoms and LiF:Mg,Cu,P TLDs", The British Journal of Radiology, 76 (2003), 232-237, by L. Duggan, et al., details dose reduction techniques for neonates in the intensive care unit. Alterations in beam energy (kVp and filtration) and collimation were investigated using specially designed phantoms mimicking a 700 g and 2000 g neonate, and ultrasensitive LiF:Mg,Cu,P thermoluminescence dosimeters. Differences in entrance surface dose (ESD) and dose at depth (3 cm or 5 cm) were compared for two overlapping fields. The reference discloses a phantom for measuring the dose profile at the surface and at different depths.

U.S. Pat. No. 6,364,529 to Dawson details a phantom for dose verification for intensity-modulated radiation therapy, comprising: a base; a static block fixed on the base; a dynamic block mounted on the base in adjustably spaced relation to the static block; at least one film divider positioned on the base between the static and dynamic blocks; and a plurality of radiation dose detectors mounted in at least one of the static and dynamic blocks. The patent further details a quality assurance phantom for multiple dosimetric devices, comprising: a pair of blocks spaced from one another and being adapted to receive radio-sensitive film there between, the blocks each having a plurality of cavities therein; and a plurality of dosimeters interchangeably mountable in the cavities of the blocks for measuring radiation dosages, wherein the dosimeters include radiochromatic film or ready pack film. This reference discloses a quality assurance phantom for multiple dosimetric devices having a pair of blocks spaced from one another and being adapted to receive radio-sensitive film there between, the blocks each having multiple cavities for mounting different dosimeters for measuring radiation dosages.

U.S. Published Patent Publication No. 2004/0228435A1 to Russell details a phantom for dose verification in intensity-modulated radiation therapy, comprising: a base of substantially tissue-equivalent material; and a two-dimensional array of cavities formed in said base with each said cavity being configured and dimensioned to receive a radiation detector. The phantom includes a base, which contains a two-dimensional, rectangular array or matrix of cavities, each cavity is dimensioned and configured for having a radiation detector inserted therein. This reference discloses a phantom for dose verification for intensity-modulated radiation therapy having a base of substantially tissue-equivalent material and a two-dimensional array of cavities formed in the base with each the cavities being configured and dimensioned to receive a radiation detector.

U.S. Pat. No. 6,225,622 to Navarro details a dynamic radiation scanning system for detecting radiation dosimetry of a beam emitted along an axis from a radiotherapy treatment machine comprising: at least one dosimetry probe constructed and arranged to sense photons and electrons; a dynamic phantom body formed from a material having a density approximating that of the human body and having a plurality of recesses for receipt of one or more of said probes therein; a gantry mounting assembly rigidly attached to said radiotherapy machine for positioning of said phantom body; and a lead screw assembly rigidly affixed to said gantry for providing coplanar movement of the dynamic phantom within a plane perpendicular to the axis of radiation emission; whereby movement of the dynamic phantom through a series of locations is carried out at varying depths so as to provide sufficient data to determine variations in beam uniformity. The dynamic phantom contains a dosimetry probe, usually an ion chamber, which may be inserted in one of several recesses, which are positioned so as to enable the user to alter the depth of the dosimetry probe within the block.

An article entitled "Multi-dimensional dosimetric verification of stereotactic radiotherapy for uveal melanoma using radiochromic EBT film", E. Sturtewagen et al., Z. Med. Phys. 18 (2008) 27-36, details a type of radiochromic film (Gafchromic EBT) for dosimetric verification with establishing a calibration curve by using films cut in squares of 2×2 cm$^2$ and positioned at 5 cm depth in a solid water phantom and irradiated with different dose levels (0.5 and 5 Gy) in a 5×5 cm$^2$ field at 6 MV.

Patent Publication No. WO 0039608 (A1) to Karger, et al., details a fixing device for dosimeter, device and method for monitoring dynamically produced spatial dose distribution. Specifically, a device for monitoring dynamically produced spatial dose distributions is provided with at least two dosimeters which are arranged on a fixing device in a defined spatial relation to one another. Said dosimeter, when mounted on an arm of a motor-driven water phantom, can be automatically positioned, their positions can be measured and saved and desired dose values can be calculated for each dosimeter.

U.S. Pat. No. 6,979,829 to Calvert et al. details determining the amount of absorbed dose during irradiation, for example during sterilization of a biological material, relating to devices and methods for determining the amount of energy absorbed during irradiation. This system utilizes alanine dosimetry however the invention is to measure absorbed radiation dose (kGy) under specified environments from −120° C. to ambient conditions.

U.S. Pat. No. 6,429,444 to Korenev et al. details real time monitoring of electron beam radiation dose and employs a processor which determines the absorbed dose of radiation absorbed by each of the first and second items, with each of the inductive detectors including a ferrite member, such as a ferrite ring. A plurality of coiled loops are mounted around a periphery of the ferrite ring.

U.S. Pat. No. 4,877,961 to McIntyre et al. details an in-line electron beam energy monitor and control, as related to charged particle accelerators and relates in particular to the energy monitoring and stabilization of charged particle beams from such accelerators without momentum analysis. A beam of charged particles is scattered by a thin foil and the flux is sampled.

An article entitled "Evaluation test of the energy monitoring device in industrial electron beam facilities", Radiation Physics and Chemistry 78 (2009) 481-484 describes a device consisting of a thick-walled (10 mm) electrically grounded aluminum cage shaped in the form of a Faraday cap. Two aluminum collector plates of different thicknesses, depending on the electron energy to be measured, are inserted into the cage separated from each other by an air gap of 5 mm and electrically insulated from the cage by ceramic posts. When the energy monitoring device was under the beam, currents, I1 from the front plate and I2 from the backplate, can be measured simultaneously.

An article entitled "Evaluation of the depth-ratio and back-scattering-factor methods in quality control measurements of electron beam energies", Applied Radiation and Isotopes 63 (2005) 217-222 details estimating the beam energy by the use of a ratio of two depth ionization measurements instead of constructing the whole depth curve. The two depths are selected on the descending part of the depth ionization curve, and the ratio of these depth readings is then related to the beam energy.

An article entitled "Dosimetry procedures in electron processing", by A. Kovacs et al., A.I.I.I Newsletter, No. 25, vol. 1-2, pp 242-251, 1992, describes use of an aluminum wedge for dosimetry of electron beam processing.

U.S. Pat. No. 7,780,352 to Fox et al., details a radiation beam quality detection method having a stepped thickness X-ray filter.

An article entitled A FULLY INTEGRATED 10 MeV ELECTRON BEAM STERILIZATION SYSTEM, by Allen et al., Radiat. Phys. Chem. Vol. 46, No. 4-6, pp. 457-460, 1995, describes penetration range measurement in an aluminum wedge.

An 11-Step, step wedge penetrometer made of aluminum used in quality assurance for medical xray applications and is available from Oprax Medical Company. The step wedge penetrometer is used for fog testing, mAs linearity, contrast vs. kVp.

U.S. Pat. No. 7,580,504 to Lang et al. details calibration devices and methods and employs a calibration phantom which includes a radioopaque step-wedge. A calibration device comprising a radioopaque material (e.g., copper or aluminum) having a stepped thickness is described. In certain embodiments, the step-wedge calibration device has equivalent bone area density coverage.

SUMMARY OF THE INVENTION

According to an embodiment of the current invention, a device and system for verifying the electron beam kinetic energy spectrum and determining changes in kinetic electron beam energy spectrum comprises a radiation-absorbing mass defined by a top surface, a bottom surface, and side walls, with said mass having at least four separate slots containing one or more of dosimeter strips, wherein said slots are located at different depths within the mass as measured from the top surface of the mass, and said slots are positioned substantially parallel to the top surface of the mass.

The radiation-absorbing material is a polymeric material, a metal, such as aluminum, or a metallic alloy. In one embodiment, the top surface of the mass is positioned facing a source of charged particles and being substantially perpendicular to direction of the charged particles emitted by the source of charged particles. In one embodiment, said mass is a substantially rectangular block, and wherein said top surface, bottom surface, and side walls are substantially rectangular. In one embodiment, the slots comprise substantially identical rectangular cutouts in the block extending from one side wall and terminating within the block, said slots adapted for positioning the dosimeter strips substantially within the middle of the block. In one embodiment, each of the slots is adapted to accept two dosimeter strips side by side, the height of the slots is adapted to preventing the dosimeter strips from overlapping, the dosimeter strips comprise alanine film dosimeters, and the strips are removable. In one embodiment, at least one slot is positioned at the depth substantially within the raising part of a radiation absorption curve, at least one slot is positioned at the depth substantially within the maximum or plateau part of the radiation absorption curve, and at least one slot is positioned substantially within the descending part of the radiation absorption curve.

In one embodiment, the block comprises a single piece of material, manufactured by machining the slots by drilling, wire discharge machining, laser drilling, electrochemical drilling, or other known techniques or combinations thereof. In one embodiment, the block is a single piece of material, manufactured by sintering of powdered material, by molding, by injection molding, by casting, or combinations thereof. In one embodiment, the block is a plurality of substantially rectangular flat plates arranged in a stack. In one embodiment, the block comprises two substantially rectangular stepped plates, adapted to mate when stepped plates are coupled together so that the stepped plates form said substantially rectangular block, with each stepped plate has at least four steps, and one of two stepped plates has at least one surface slot machined into each step. Two stepped plates when assembled are optionally permanently or temporarily joined by an external bracket, an adhesive, diffusion bonding, an adhesive tape, rivets, fasteners, pins, screws, bolts, or combinations thereof.

In one embodiment, device and system for verifying the electron beam kinetic energy spectrum and determining changes in kinetic electron beam energy spectrum further includes an electron beam radiation source, and a conveyor for moving the device past the radiation source. In one embodiment, a device and system for verifying the electron beam kinetic energy spectrum and determining changes in kinetic electron beam energy spectrum comprises an electron beam radiation source, a device comprising a mass having a known density, length, width, thickness and atomic composition, at least four slots within the device, each slot being located at a unique depth and length-width coordinate, dosimeters located within the slots, and a conveyor for moving the device and dosimeters past the radiation source.

In one embodiment, a method of determining and comparing changes in a kinetic electron energy spectrum comprises the steps of:

providing a device comprising a radiation-absorbing mass defined by a top surface, a bottom surface, and side walls, said mass having at least four separate slots containing one or more of dosimeter strips, wherein said slots are located at different depths within the mass as measured from the top surface of the mass, and said slots are positioned substantially parallel to the top surface of the mass, moving the device containing a first set of dosimeters past a radiation source exposing the device containing dosimeters to a defined energy spectrum for a time sufficient to affect the first set of dosimeters, moving the device containing a second set of dosimeters, past the radiation source exposing the device containing dosimeters to the defined energy spectrum for a time sufficient to affect the second set of dosimeters, measuring radiation absorbed doses by each set of dosimeters, calculating specific dose response ratios, for each set of dosimeters, and comparing the dose response ratios calculated for the first set of dosimeter readings to dose response ratios calculated for the second set of dosimeters.

DETAILED DESCRIPTION OF THE INVENTION

Figure 1:
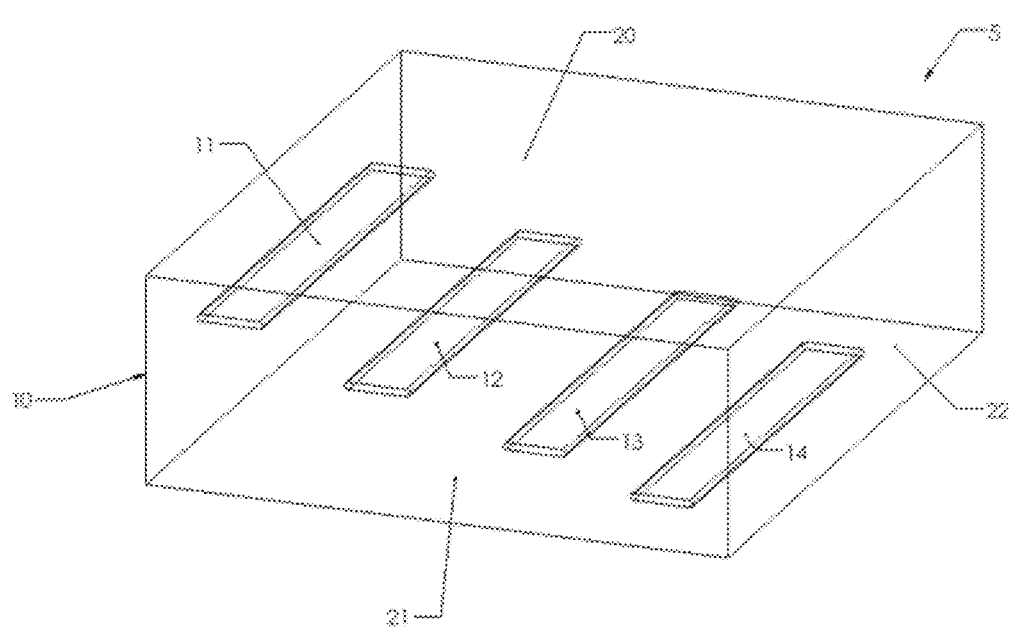
FIG. 1 shows a three-dimensional view of an embodiment of the present invention

There is provided a system that is directly tied to radiation physics so the dosimeter placement pattern is permanently defined in order to estimate changes in the electron beam spectra. The data comparisons will support current processing relative to the last formal validation and/or revalidation event. The system is able to monitor and diagnose potential changes on a more frequent or routine and simplified basis while avoiding the expense, time constraints and difficulty of mobility of the known and the current art of electron beam energy measurement. The technology is not requiring a calibration event, calibration curve, examination of response function, and formal acceptance and verification. The instant system does not need to actually measure the absorbed dose. The verification/monitoring step is extremely fast and very low cost to the end-user or the irradiation facility.

It is one of the objectives of the present invention to efficiently and accurately verify kinetic energy spectrum, and determine changes in the kinetic energy spectrum of accelerated electrons applied to a product to ensure product safety, efficacy and to aid as a quality control check of the controlled irradiation (sterilization) process. It is one of the objectives of the present invention to provide for low cost effective system to monitor and verify the electron beam energy without taking a direct measurement of electron energy.

According to an embodiment of the present invention, a method and device is provided to (a) verify known electron energy spectrum, (b) allow the end-user to monitor the electron energy spectrum and (c) determine changes in electron kinetic energy spectra. The device enables the end-user to quickly and effectively monitor changes in the electron kinetic energy spectrum thereby ensuring radiation-processed product efficacy and safety. In one embodiment, the device performs the "check-standard" function. The device's absorbed dose output directly tied to national and international standards of absorbed dose through the application of a calibrated alanine/epr dosimetry system.

According to an embodiment of the present invention, the device or phantom is a stepped design, with alanine dosimeters placed at specific and predetermined depths in a metallic-alloy or polymeric device. The placement of the dosimeters is based on Monte Carlo calculations directly tied to the device's geometry, atomic composition, density and calculated depth-dose profile within the device material selected. The device is loaded with alanine dosimeters at calculated depths within the device and it is irradiated. The depths of the recesses in the design are directly tied to radiation physics identified through the use of Monte-Carlo calculations. The recesses in the design, through mathematical simulation and modeling, can be changed based on the device's density, atomic composition, intended electron beam spectra, etc. Following irradiation, the dosimeters are measured, and a ratio is developed between each dosimeter position within the device design. These ratios are critical to the successful verification of energy spectrum and determination of potential change in the kinetic energy spectrum. The ratio to each dosimeter is critical since a change in the kinetic energy spectrum will result in a change in the ratio. This "check standard" approach can be rapid in terms of analysis and subsequent verification and determination of electron energy spectrum. This "check standard" will enable the end-user to document changes in energy spectrum in between formal energy measurements. Use of this methodology will ensure the energy spectrum is maintained that is directly tied to dose mapping activities and can be used in a variety of irradiation designs over a broad range of energy spectra.

This invention enables the end-user to document changes in electron energy spectrum. This technique and related methodology can be utilized on a run-to-run, daily or weekly basis, due to its low cost and simple design. Use of this methodology ensures that the electron energy spectrum is maintained as a constant during radiation processing, and as such, is directly tied to absorbed dose mapping activities associated with product qualification and radiation process validation/revalidation. This technology can be used in a variety of irradiation designs, over a broad range of electron energy spectra, at a variety of absorbed dose rates.

By application of the instant device, a verification of electron kinetic energy spectrum can be performed in approximately ten to fifteen minutes. Given its short analysis interval, this verification device and its associated test(s) can be used to ensure consistency of electron energy spectrum on a frequent basis (e.g. daily or even more frequently). As a quality assurance device, the device can verify and monitor potential change. If a change is indicated, then an actual electron energy measurement can be made. The device can be used to lengthen the time interval between formal electron energy measurements thereby saving costs while ensuring the operating environment does not deviate from that, which existed during the original validation. As a result of the modified design, the device can be used routinely unlike formal energy measurements, which are performed on a monthly or quarterly basis.

According to an embodiment of the present invention, the present device can be used for the monitoring of the kinetic energy spectrum of charged particles and generated photons. Following the commissioning of an industrial irradiator, kinetic energy measurements are taken on a very infrequent basis (e.g. quarterly, biannually, and annually). The measurement of the kinetic energy, for example, with accelerated electrons from 300 keV and 25 MeV, is a time consuming/labor intensive activity. Therefore, this important parameter is only sparsely examined. The kinetic energy spectrum, however, is directly tied to the dose mapping activity, which ensures product efficacy and safety due the absorbed dose contribution in the depth-dose curve.

The device of the present invention does not measure the kinetic energy spectrum. It is designed to monitor changes in the kinetic energy spectrum in-between formal energy measurements. The device enables the end-user to quickly and effectively monitor changes in the kinetic energy spectrum thereby ensuring product efficacy and safety. All analytical instruments have "check-standards" to verify and monitor performance. This device performs the same "check-standard" function with its output directly tied to national and international standards to the measurement of absorbed dose by the application of the alanine dosimetry system.

According to an embodiment of the present invention, the use of Alanine Dosimetry/Dosimeter provides for accuracy in measurement and stability of dosimeter material. The monitoring of energy generated from charged particles and generated photons provides for timely alerts to fluctuating energy levels and for verification and monitoring of performance to ensure product safety and efficacy. The verification of energy ensures achieving the desired irradiation dose to materials, thus providing protection to radiation sensitive materials. The verification of energy is necessary for use in irradiation system optimization.

The instant device and method allows for facility/QA driven check program, with uncomplicated data acquisition and analysis; and provides for repeatable reproducible data collection with no calibration requirements, if desired.

The instant device and method could be used for sterilization process control. It can be used with any accelerator design to monitor energy and can provide direct traceability to national and international standards. The device has a flexible functional energy range and can be used to assess wide range of energies based on dosimetry placement with the stepped design in a variety of phantom materials.

The instant device and method is cost effective and the device withstands indefinite repeated irradiations, with dosimeters being the sole consumable item. According to the present device/method, the test is performed at low target dose to minimize irradiation time. The present device/method is multi-purpose and enables comparative evaluation of energies between modalities, machines, time intervals, with a short test time and time to results with the possibility of impromptu system check, audit, and troubleshooting.

Figure 2:
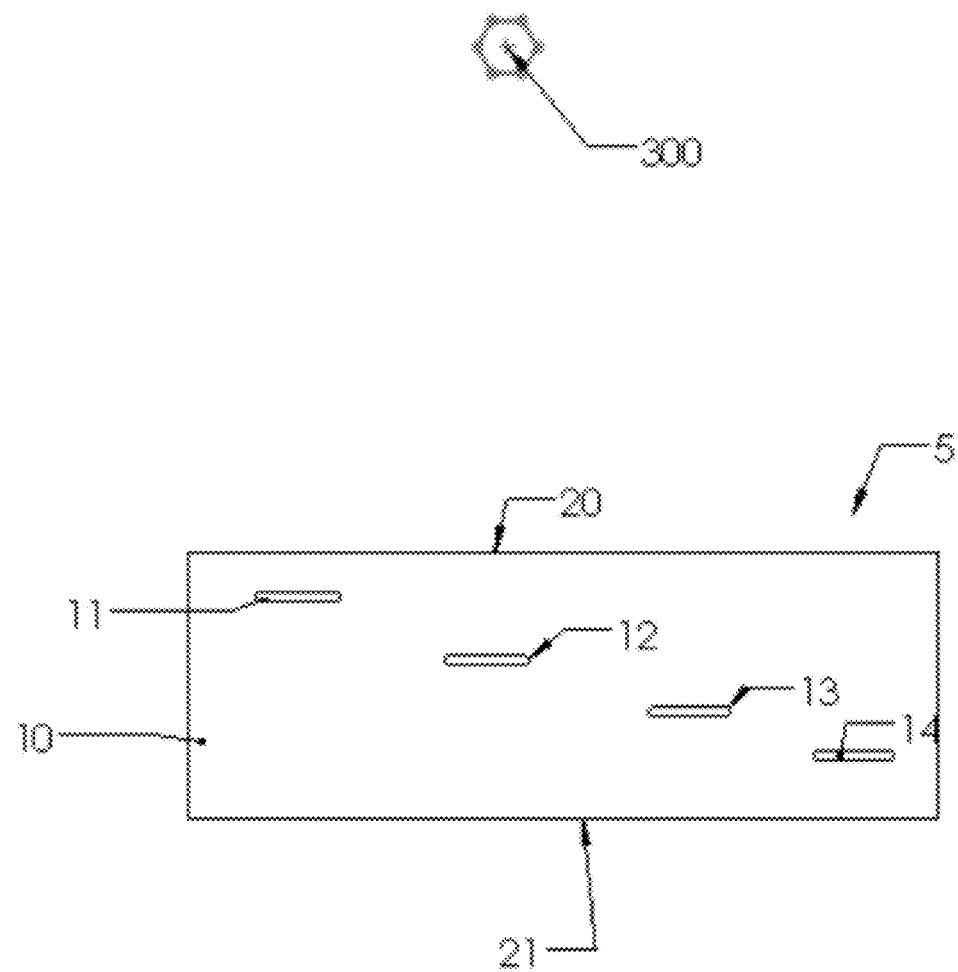
FIG. 2 shows a side view of an embodiment of the present invention
Figure 3:
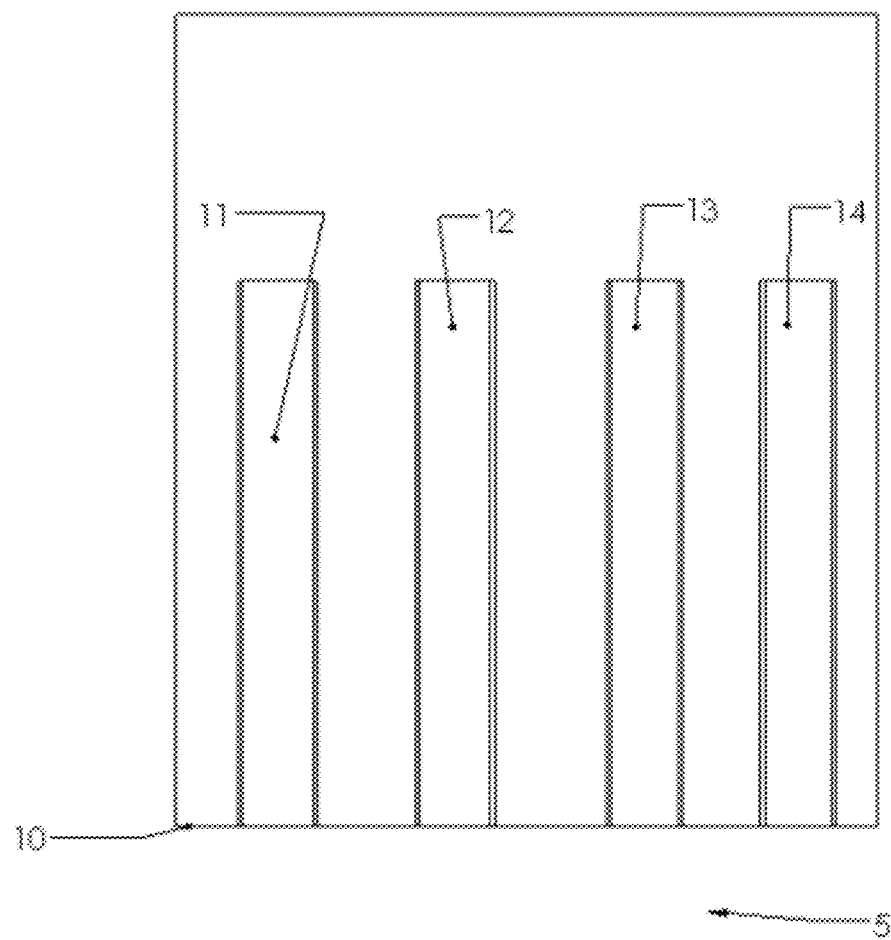
FIG. 3 shows a top cross-sectional view of an embodiment of the present invention

Referring now to FIGS. 1, 2, and 3, representing a three-dimensional view, a side view, and a top cross-sectional view of an embodiment of the present invention, the device 5 comprises a mass such as a generally rectangular block 10 defined by top surface 20 and bottom surface 21 and side walls 22, with a plurality of slots 11, 12, 13, and 14 located at different depths within block 10 as measured from the top surface 20 of the block 10. At least three slots are provided, with four slots 11, 12, 13, and 14 shown in the embodiment of FIG. 1.

Block 10 is made of radiation-absorbing material, which can be a polymeric material or a metal, such as aluminum, with the material selected depending on the time of the irradiation and the kinetic energy of charged particles and generated photons. In one embodiment, block 10 is made of 1100 series aluminum (minimum 99% Al), in another embodiment, block 10 is made of 6061 series aluminum alloy (minimum 95% Al).

Higher kinetic energy will require more absorbent material or an increase of the density of the absorbing material of block 10 and repositioning of slots 11, 12, 13, and 14 within block 10 as measured from top surface 20 based on the Monte Carlo predictions. Top surface 20 is the surface of block 10 which is preferably positioned facing a source of the charged particles 300, being substantially perpendicular to direction of charged particles emitted by source 300 and entering block 10.

Figure 4:
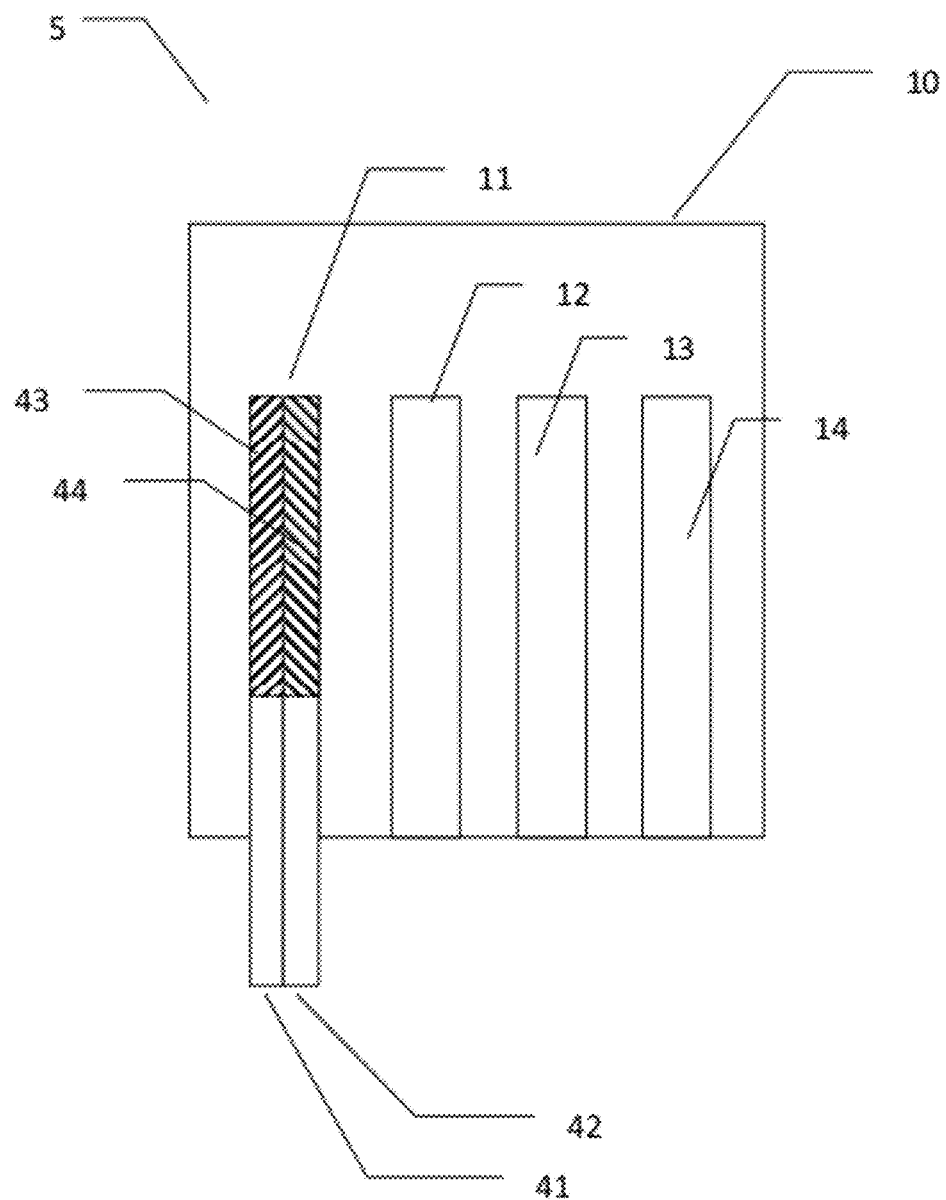
FIG. 4, shows a top cross-sectional view of an embodiment of the present invention

Referring now to FIG. 4, representing top cross-sectional view, slots 11, 12, 13, and 14 are adapted for insertion of dosimeter strips and have width to accommodate one or more strips and heights to enable insertion of strips. Slots 11, 12, 13, and 14 are substantially identical in shape and comprise rectangular cuts-outs in block 10 extending from side wall 22 and parallel to top surface 20, terminating within block 10 so that dosimeter strips are positioned substantially within the middle of block 10 being parallel to top surface 20. As shown in FIG. 4, in a preferred embodiment, slot shape is adapted to accept two dosimeter strips 41 and 42 side by side (shown in inserted slot 11), with the height of the slot preventing strips to overlap. The sensitive part of dosimeter strips 41 and 42 is schematically patterned and indicated by numerals 43 and 44 is substantially within block 10.

Figure 5:
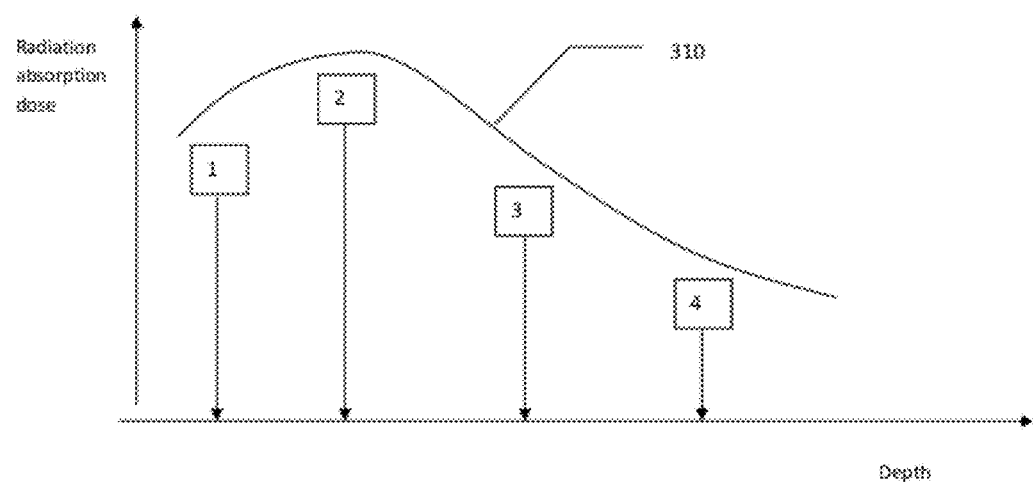
FIG. 5 shows a typical radiation absorption curve in coordinates dose vs. depth in the material

Slots 11, 12, 13, and 14, also referred to as dosimeter positions 1, 2, 3, and 4, are positioned between top surface 20 and bottom surface 21 at different depths from top surface 20 of the block 10, with slots being substantially parallel to top surface 20. Depths of positioning of slots 11, 12, 13, and 14 or distance of slots 11, 12, 13, and 14 from top surface 20 is determined based on the radiation absorption curves for a given kinetic energy of source 300, time of exposure, and type of material. Based on any published depth-dose curve and Monte Carlo simulation by changing the material of the device or phantom, depth and corresponding design. Referring now also to FIG. 5, showing a typical radiation absorption curve 310 in coordinates dose vs. depth in the material, it is illustrated that the depth of positioning of Slots 11, 12, 13, and 14 is selected so that slot 11 is positioned to be at the depth substantially within the raising part of the radiation absorption curve 310, slot 12 is positioned substantially within the maximum or plateau part of the radiation absorption curve 310, slot 13 and slot 14 are positioned substantially within the descending part of the radiation absorption curve 310.

Minimum of three slots 11, 12, and 13 are present in device 5. In a preferred embodiment there are four slots as shown in FIGS. 1-3. In another embodiment of the invention, up to 10 or up to 20 or more slots can be present based on the Monte Carlo predictions, with some slots occurring at the same depth as others, with some slots being at the depth substantially within the raising part of the radiation absorption curve 310, some slots substantially within the maximum or plateau part of the radiation absorption curve 310, some slots substantially within the descending part of the radiation absorption curve 310.

In one embodiment, device 5 is made out of a single block of material by machining slots 11, 12, 13, and 14 by drilling, wire discharge machining, laser drilling, electrochemical drilling, other known techniques or combinations thereof. In another embodiment device 5 is made by sintering of powdered material or by molding, injection molding, or by casting.

Figure 6:
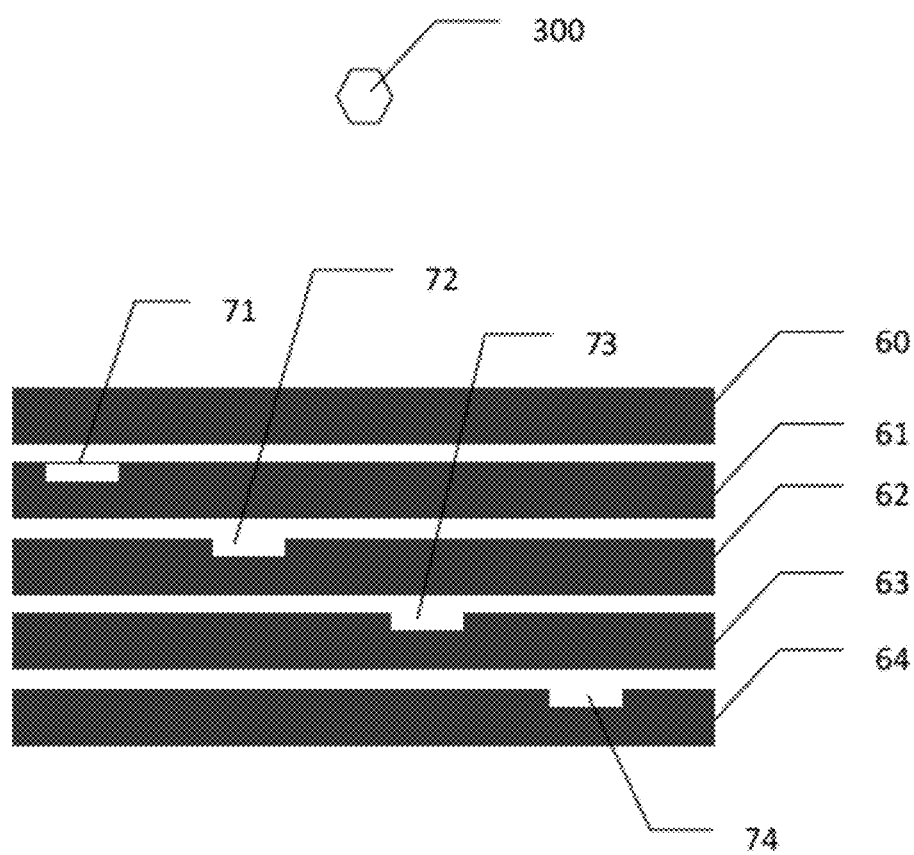
FIG. 6 shows a side view of an embodiment of the present invention
Figure 7:
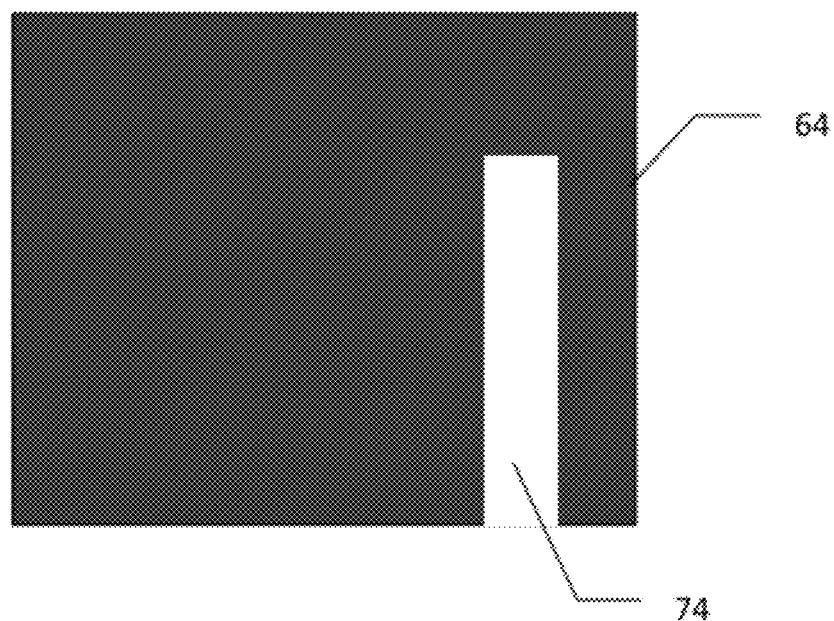
FIG. 7 shows a top view of flat plate with surface slot according to an embodiment of the present invention

In one embodiment, device 5 is made of a plurality of substantially rectangular flat metallic plates arranged in a stack or deck, with at least three of the plates having surface slots machined therein. When assembled as a stack, the flat plates can be permanently or temporarily joined by external brackets, adhesive, diffusion bonding, adhesive tape, rivets, or fasteners, such as pins, screws or bolts, to form a fixed stack or deck with slots 11, 12, 13, and 14 preferably open from the same side. Referring now to FIG. 6, showing a side view, in one embodiment, device 5 comprises a stack of five flat substantially rectangular plates 60, 61, 62, 63, and 64, with four flat plates 61, 62, 63, 64, having a surface slot 71, 72, 73, 74 machined therein and top flat plate 60 having no slot therein. The position of surface slots 71, 72, 73, 74 is selected so as to prevent any overlapping of slot positions with respect to the position of source of the charged particles 300. Referring now to FIG. 7, a top view of flat plate 64 with surface slot 74 is shown.

In one embodiment, device 5 is a stack of 15 flat sheets of 1100 series aluminum (minimum 99% Al) sized 14.5 cm×14.5 cm×0.2 cm, with the total size of the rectangular stack is 14.5 cm×14.5 cm×3 cm. Of these 15 sheets, 4 have machined surface channels which, when stacked with solid sheets, form slots 1.1 cm wide of 0.05 cm depth to accommodate dosimeter strips with no resistance. In one embodiment, the slots are designed to accommodate 2 KODAK BIOMAX alanine film dosimeters.

Figure 8:
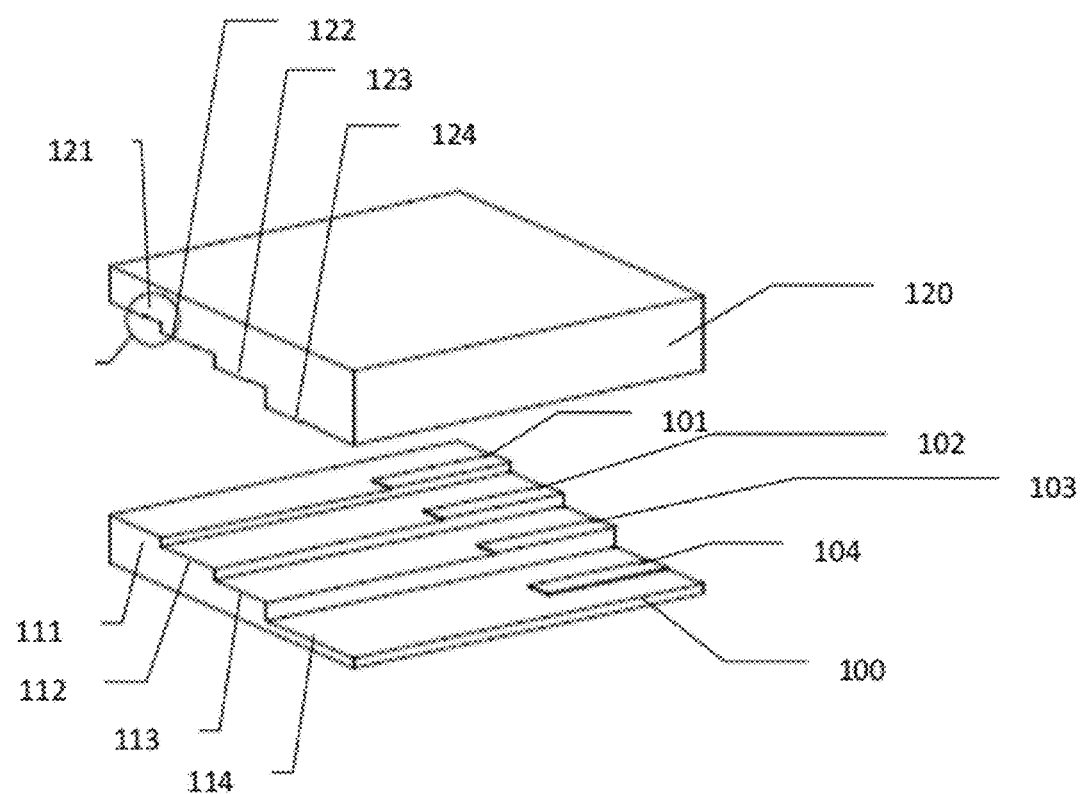
FIG. 8 shows a three-dimensional view of an embodiment of the present invention prior to assembly
Figure 9:
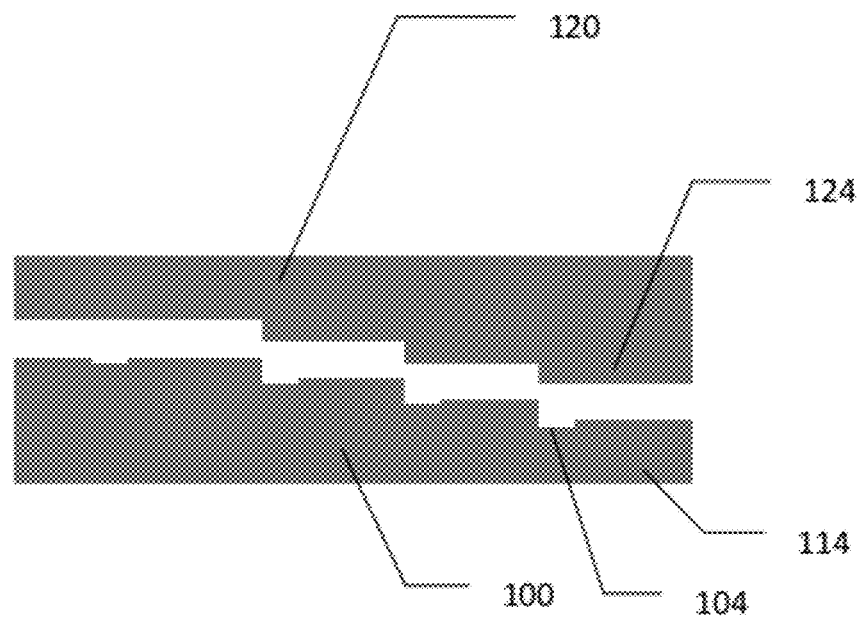
FIG. 9 shows a side view of an embodiment of the present invention prior to assembly
Figure 10:
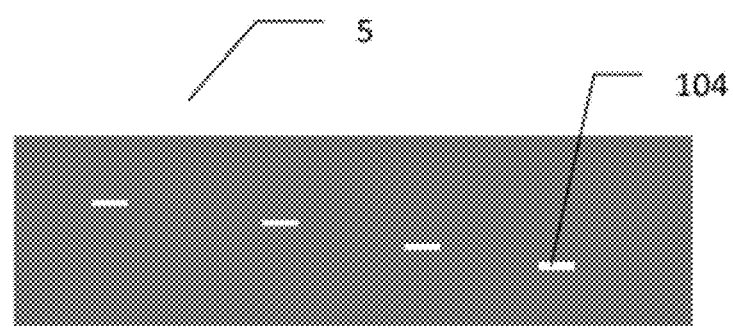
FIG. 10 shows a side view of an embodiment of the present invention after assembly

Referring now to FIG. 8, an embodiment of the present invention comprises device 5 made of two substantially rectangular stepped plates 100 and 120, having steps 111, 112, 113, 114 on stepped plate 100 and steps 121, 122, 123, 124 on stepped plate 120. Surface slots 101, 102, 103, 104 are machined in steps 111, 112, 113, 114. Referring to FIGS. 9 and 10, representing side view of stepped plates 100 and 120, dimensions of steps 111, 112, 113, 114 on stepped plate 100 and steps 121, 122, 123, 124 on stepped plate 120 are adapted to mate when stepped plates 100 and 120 are coupled together so that stepped plates 100 and 120 form a substantially rectangular device 5. When assembled, stepped plates 100 and 120 can be permanently or temporarily joined by external brackets, adhesive, diffusion bonding, adhesive tape, rivets, or fasteners, such as pins, screws or bolts. In one embodiment, stepped plates 100 and 120 are made of 6061 series aluminum alloy (minimum 95% Al), with machined surface channels in one piece forming slots when second piece is fitted in place. The channel spacing can be optimized for a variety of charged particles and energy spectra from 2 to 12 MeV.

In all embodiments of device 5, dosimeters are placed in the device so that each dosimeter does not fall within the pathway between the source of radiation and the other dosimeters held within the device, and with dosimeters being at an orientation substantially perpendicular to the direction of energy applied to the device. This additionally eliminates the error in dosimeter readings at their given positions due to the non-homogeneous nature of the material through which the radiation passes to reach the dosimeter as the radiation passes through the device material which has different energy absorption characteristics than the material used in the dosimeters. Perpendicular orientation assures that the dosimeters record the reading at a specific plane within the device. In all embodiments, each dosimeter strip is always perpendicular to the source. Discrete steps of the locations of dosimeter strips in the inventive device 5 provide for high precision, well defined positions to characterize energy deposition and to compare energy deposition between different accelerators or within one accelerator at different operational parameters, on different days, shifts, etc, instead of measuring energy as it is done in known techniques such as wedge-based techniques. The use of the inventive device allows for faster comparison of energy parameters of accelerators by less skilled operators relative to the known aluminum wedge technology.

Example 1

Figure 11:
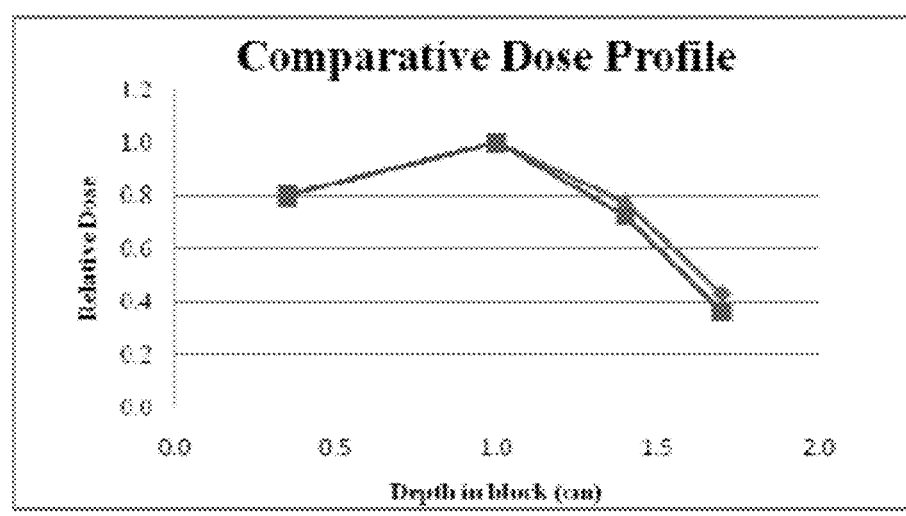
FIG. 11 shows a graph representing comparative dose profile for two electron accelerators as relative dose vs. depth

Experimental Irradiation Absorbed Dose Measurements for two different accelerators are presented in Tables 1 and 2, using the device comprising two stepped plates. Referring now to graph shown in FIG. 11, comparative dose profile for two electron accelerators is shown as relative dose relative to depth aluminum block of the inventive device 5, with large squares corresponding to accelerator IBA Rhodotron TT100 #2, calibrated by conventional wedge technologies as 10.0 MeV, and with smaller rhombs corresponding to accelerator IBA TT00 #1, calibrated by conventional wedge technologies as 10.4 MeV. The graph shown in FIG. 11 and Tables reflect kinetic energy differences between two electron accelerators with primary kinetic energy differences of only 4% as measured by conventional wedge technologies: IBA TT00 #1: 10.4 MeV; IBA Rhodotron TT100 #2: 10.0 MeV.

Using the present device and method, looking at the mean dose ratio in scaled results, especially at positions 3 and 4, one can see and detect differences between two accelerators with primary kinetic energy differences being as small as 4% (based on standard conventional wedge technology based calibration). The graph shown in FIG. 11 and Tables 1-2 illustrate that the instant method and device are capable of detecting even small differences in energies of two systems. Specifically, the instant invention enabled detection of differences as small as 4% between accelerators or at different regimes of the same accelerator, without using expensive and time-consuming conventional wedge technology measurements. The data collected, using the present method and device, indicate, independently, that energy of Accelerator #1 is 4% greater than that of Accelerator #2. Ratios of absorbed dose per position are independent of the duration of exposure.

TABLE 1

Experimental Dose Measurements, Accelerator ID: IBA #1
Experimental Dose Measurements, kGy, Accelerator ID: IBA #1

| Position | Depth in Al Block (cm) | Test 1 | Test 2 | Test 3 | Test 4 | Test 5 | Test 6 | Test 7 | Test 8 | Test 9 | Mean |
|---|---|---|---|---|---|---|---|---|---|---|---|
| 1 | 0.4 | 2.92 | 2.94 | 2.95 | 3.01 | 3.00 | 2.98 | 3.19 | 3.09 | 3.17 | |
| 2 | 1.0 | 3.61 | 3.62 | 3.65 | 3.81 | 3.97 | 3.73 | 4.02 | 3.97 | 3.91 | |
| 3 | 1.4 | 2.82 | 2.83 | 2.80 | 2.92 | 2.89 | 2.91 | 3.02 | 3.13 | 3.06 | |
| 4 | 1.7 | 1.60 | 1.59 | 1.58 | 1.62 | 1.59 | 1.59 | 1.72 | 1.67 | 1.69 | |
| Results Scaled to Position 2 | | | | | | | | | | | |
| 1 | 0.4 | 0.81 | 0.81 | 0.81 | 0.79 | 0.79 | 0.80 | 0.79 | 0.78 | 0.81 | 0.80 |
| 2 | 1.0 | 1.00 | 1.00 | 1.00 | 1.00 | 1.00 | 1.00 | 1.00 | 1.00 | 1.00 | 1.00 |
| 3 | 1.4 | 0.78 | 0.78 | 0.77 | 0.77 | 0.76 | 0.78 | 0.75 | 0.79 | 0.78 | 0.77 |
| 4 | 1.7 | 0.44 | 0.44 | 0.43 | 0.43 | 0.42 | 0.43 | 0.43 | 0.42 | 0.43 | 0.43 |

TABLE 2

Experimental Dose Measurements, Accelerator ID: IBA #2
Experimental Dose Measurements, kGy, Accelerator ID: IBA #2

| Position | Depth in Al block (cm) | Test 1 | Test 2 | Test 3 | Test 4 | Test 5 | Test 6 | Test 7 | Test 8 | Test 9 | Mean |
|---|---|---|---|---|---|---|---|---|---|---|---|
| 1 | 0.4 | 3.15 | 3.22 | 3.26 | 3.43 | 3.38 | 3.39 | 3.20 | 3.20 | 3.23 | |
| 2 | 1.0 | 4.01 | 4.05 | 4.04 | 4.31 | 4.19 | 4.22 | 4.00 | 4.02 | 4.07 | |
| 3 | 1.4 | 2.91 | 2.95 | 2.95 | 3.15 | 3.02 | 3.06 | 2.88 | 2.90 | 2.90 | |
| 4 | 1.7 | 1.46 | 1.49 | 1.50 | 1.56 | 1.47 | 1.50 | 1.41 | 1.42 | 1.41 | |
| Results Scaled to Position 2 | | | | | | | | | | | |
| 1 | 0.4 | 0.78 | 0.80 | 0.81 | 0.80 | 0.81 | 0.80 | 0.80 | 0.80 | 0.79 | 0.80 |
| 2 | 1.0 | 1.00 | 1.00 | 1.00 | 1.00 | 1.00 | 1.00 | 1.00 | 1.00 | 1.00 | 1.00 |
| 3 | 1.4 | 0.73 | 0.73 | 0.73 | 0.73 | 0.72 | 0.72 | 0.72 | 0.72 | 0.71 | 0.72 |
| 4 | 1.7 | 0.36 | 0.37 | 0.37 | 0.36 | 0.35 | 0.35 | 0.35 | 0.35 | 0.35 | 0.36 |

Example 2

Results of experiments with device comprising two stepped plates over seven days are presented in Tables 3-5

TABLE 3

Experimental Dose Measurements, kGy, Days 1-2

| Position | Depth in Al block (cm) | Day 1 | | | Day 2 | | |
|---|---|---|---|---|---|---|---|
| | | Test 111009-1 kGy | Test 111009-2 kGy | Test 111009-3 kGy | Test 111109-1 kGy | Test 111109-2 kGy | Test 111109-3 kGy |
| 1 | 0.4 | 3.10 | 3.15 | 3.07 | 3.13 | 3.16 | 3.12 |
| 2 | 1.0 | 3.90 | 3.90 | 3.92 | 3.92 | 3.95 | 3.96 |
| 3 | 1.4 | 2.95 | 2.96 | 2.99 | 3.04 | 3.05 | 3.10 |
| 4 | 1.7 | 1.65 | 1.65 | 1.65 | 1.70 | 1.70 | 1.72 |
| | | Results scaled to position 2 | | | | | |
| 1 | 0.4 | 0.79 | 0.81 | 0.78 | 0.80 | 0.80 | 0.79 |
| 2 | 1.0 | 1.00 | 1.00 | 1.00 | 1.00 | 1.00 | 1.00 |
| 3 | 1.4 | 0.76 | 0.76 | 0.76 | 0.77 | 0.77 | 0.78 |
| 4 | 1.7 | 0.42 | 0.42 | 0.42 | 0.43 | 0.43 | 0.43 |

TABLE 4

Experimental Dose Measurements, Days 3-5

| Position | Depth in Al block (cm) | Day 3 | | | Day 4 | Day 5 | |
|---|---|---|---|---|---|---|---|
| | | 111209-1 kGy | 111209-2 kGy | 111209-3 kGy | 111609-1 kGy | 111709-1 kGy | 111709-2 kGy |
| 1 | 0.4 | 2.97 | 2.97 | 2.98 | 2.97 | 3.01 | 2.95 |
| 2 | 1.0 | 3.74 | 3.76 | 3.81 | 3.72 | 3.87 | 3.81 |
| 3 | 1.4 | 2.89 | 2.95 | 2.92 | 2.87 | 2.99 | 2.92 |
| 4 | 1.7 | 1.61 | 1.64 | 1.70 | 1.66 | 1.70 | 1.68 |
| | | Results scaled to position 2 | | | | | |
| 1 | 0.4 | 0.79 | 0.79 | 0.78 | 0.80 | 0.78 | 0.77 |
| 2 | 1.0 | 1.00 | 1.00 | 1.00 | 1.00 | 1.00 | 1.00 |
| 3 | 1.4 | 0.77 | 0.78 | 0.77 | 0.77 | 0.77 | 0.77 |
| 4 | 1.7 | 0.43 | 0.44 | 0.45 | 0.45 | 0.44 | 0.44 |

TABLE 5

Experimental Dose Measurements, Days 6-7

| Position | Depth in Al block, cm | Day 6 | | | Day 7 | | | | | |
|---|---|---|---|---|---|---|---|---|---|---|
| | | 120109-1 kGy | 120109-2 kGy | 120109-3 kGy | 120209-1 kGy | 120209-2 kGy | 120209-3 kGy | 120209-4 kGy | 120209-5 kGy | 120209-6 kGy |
| 1 | 0.4 | 2.92 | 2.94 | 2.95 | 3.01 | 3.00 | 2.98 | 3.19 | 3.09 | 3.17 |
| 2 | 1.00 | 3.61 | 3.62 | 3.65 | 3.81 | 3.79 | 3.73 | 4.02 | 3.97 | 3.91 |
| 3 | 1.40 | 2.82 | 2.83 | 2.80 | 2.92 | 2.89 | 2.91 | 3.02 | 3.13 | 3.06 |
| 4 | 1.70 | 1.60 | 1.59 | 1.58 | 1.62 | 1.59 | 1.59 | 1.72 | 1.67 | 1.69 |
| Position | | Results scaled to position 2 | | | | | | | | |
| 1 | 0.4 | 0.81 | 0.81 | 0.81 | 0.79 | 0.79 | 0.80 | 0.79 | 0.78 | 0.81 |
| 2 | 1.00 | 1.00 | 1.00 | 1.00 | 1.00 | 1.00 | 1.00 | 1.00 | 1.00 | 1.00 |
| 3 | 1.40 | 0.78 | 0.78 | 0.77 | 0.77 | 0.76 | 0.78 | 0.75 | 0.79 | 0.78 |
| 4 | 1.70 | 0.44 | 0.44 | 0.43 | 0.43 | 0.42 | 0.43 | 0.43 | 0.42 | 0.43 |

Example 3

Summary of the results of 21 tests performed on 7 different days by 4 different associates is presented in Table 6, with the data extracted from Tables 3-5. Data of Table 6 shows that the results are repeatable and reproducible. CV stands for Coefficient of Variation (std dev divided by the average value)

TABLE 6

Experimental Dose Measurements summary

|  | Day 1 | Day 2 | Day 3 | Day 4 | Day 5 | Day 6 | Day 7 | Overall | |
| --- | --- | --- | --- | --- | --- | --- | --- | --- | --- |
| Position 1 | 0.79 | 0.80 | 0.79 | 0.80 | 0.77 | 0.81 | 0.79 | 0.79 | Mean |
|  | 1.2% | 0.7% | 0.6% | NA | 0.3% | 0.2% | 1.1% | 1.1% | CV |
| Position 2 | 1.00 | 1.00 | 1.00 | 1.00 | 1.00 | 1.00 | 1.00 | 1.00 | Mean |
|  | 0.0% | 0.0% | 0.0% | 0.0% | 0.0% | 0.0% | 0.0% | 0.0% | CV |
| Position 3 | 0.76 | 0.78 | 0.77 | 0.77 | 0.77 | 0.78 | 0.77 | 0.77 | Mean |
|  | 0.2% | 0.5% | 1.0% | NA | 0.4% | 0.8% | 1.4% | 1.0% | CV |
| Position 4 | 0.42 | 0.43 | 0.44 | 0.45 | 0.44 | 0.44 | 0.43 | 0.43 | Mean |
|  | 0.1% | 0.1% | 0.8% | NA | 0.0% | 0.6% | 0.5% | 0.8% | CV |

Example 4

Procedures for using the device and method of the present invention. According to an embodiment of the present invention, the process of using the using the device and method is outlined below.

Assemble two substantially rectangular stepped plates 100 and 120 so that stepped plates 100 and 120 form a substantially rectangular device, as shown in FIGS. 8, 9, 10. Ensure that the pieces are aligned and the block is squared. Secure with non-metallic tape such as masking tape.

Label eight alanine film dosimeters to identify their position in the device and insert the alanine film dosimeters into the slots, two alanine film dosimeters per slot side by side.

Position the device with top surface facing a source of the charged particles, being substantially perpendicular to direction of charged particles. Optionally the device can be placed into a holding jig for ease of maneuvering and re-positioning. Optionally secure the device within the holding jig by non-metallic tape.

Measure the temperature of the device by placing a thermocouple into one of the slots to determine the internal temperature or by using an instrument such as an IR gun to measure the surface temperature.

Obtain the accelerator system settings to yield a target absorbed dose to the dosimeters of 3 kGy or a dose in the linear part of the dosimeter calibration curve.

Place the device on the conveyor positioned to irradiate the front (top) surface of the device facing the beam source. The device is transported through the process with the electron beam entering the front (top) surface of the device and exiting the back (bottom) surface of the device.

Upon completion of irradiation, measure the device temperature by the same means as was done initially. Calculate the temperature increase based on the previously recorded starting temperature. Check the dosimeter manufacturer's specifications to ensure that the increase is not beyond the tolerance of the dosimeter strip.

Remove the dosimeter films from the device. Measure the response of each dosimeter using a calibrated dosimetry system and, if required, calculate the response into absorbed dose. Determine the mean response or absorbed dose at positions 1 through 4 by averaging the measurements of both dosimeter films in each slot. Compare the following ratios of mean position measurements:

Position 1:Position 2
Position 2:Position 2
Position 3:Position 2
Position 4:Position 2

Table 7 lists an example of doses and ratios that might result from this experiment.

| Position | Dose in kGy | Position | Ratio |
| --- | --- | --- | --- |
| 1 | 3.15 | 1 | 3.15/4.01 = 0.78 |
| 2 | 4.01 | 2 | 4.01/4.01 = 1.00 |
| 3 | 2.91 | 3 | 2.91/4.01 = 0.73 |
| 4 | 1.46 | 4 | 1.46/4.01 = 0.36 |

Compare these resulting ratios to past/future results to determine if the kinetic energies of the tested systems are different.
a) Compare multiple systems
b) Compare the same system over time
c) Compare the same system before/after some change Table 8 presents an example of a comparison of two different systems. The systems' energies were determined prior to experimentation by standard aluminum wedge experiments.

TABLE 8

| Position | Ratio |
| --- | --- |
| System #1 Wedge Energy = 10.4 MeV | |
| 1 | 0.81 |
| 2 | 1.00 |
| 3 | 0.78 |
| 4 | 0.44 |
| System #2 Wedge Energy = 10.0 MeV | |
| 1 | 0.78 |
| 2 | 1.00 |
| 3 | 0.73 |
| 4 | 0.36 |

We claim:
1. A method of determining and comparing changes in a kinetic electron energy spectrum comprising the steps of:
providing a device comprising a radiation-absorbing mass defined by a top surface, a bottom surface, and side walls, said mass having at least four separate slots containing one or more of dosimeter strips, wherein said slots are located at different depths within the mass as measured from the top surface of the mass, and said slots are positioned substantially parallel to the top surface of the mass, moving the device containing a first set of dosimeters past a radiation source exposing the device containing dosimeters to a defined energy spectrum for a time sufficient to affect the first set of dosimeters, moving the device containing a second set of dosimeters, past the radiation source exposing the device containing dosimeters to the defined energy spectrum for a time sufficient to affect the second set of dosimeters, measuring radiation absorbed doses by each set of dosimeters, calculating specific dose response ratios, for each set of dosimeters, and comparing the dose response ratios calculated for the first set of dosimeter readings to dose response ratios calculated for the second set of dosimeters.

2. The method of claim 1, wherein said radiation-absorbing mass is a polymeric material, a metal, or a metallic alloy.

3. The method of claim 2, wherein said radiation-absorbing mass is aluminum.

4. The method of claim 3, wherein the top surface of the mass is positioned facing a source of charged particles and being substantially perpendicular to direction of the charged particles emitted by the source of charged particles.

5. The method of claim 4, wherein said mass comprises a substantially rectangular block, and wherein said top surface, bottom surface, and side walls are substantially rectangular.

6. The method of claim 5, wherein said slots comprise substantially identical rectangular cutouts in the block extending from one side wall and terminating within the block, said slots adapted for positioning the dosimeter strips substantially within the middle of the block.

7. The method of claim 6, wherein each of the slots is adapted to accept two dosimeter strips side by side, wherein the height of the slots is adapted to preventing the dosimeter strips from overlapping, wherein the dosimeter strips comprise alanine film dosimeters, and wherein said strips are removable.

8. The method of claim 7, wherein at least one slot is positioned at the depth substantially within the raising part of a radiation absorption curve, at least one slot is positioned at the depth substantially within the maximum or plateau part of the radiation absorption curve, and at least one slot is positioned substantially within the descending part of the radiation absorption curve.

9. The method of claim 8, wherein the block comprises a single piece of material, said block manufactured by machining the slots by drilling, wire discharge machining, laser drilling, electrochemical drilling, or other known techniques or combinations thereof.

10. The method of claim 8, wherein the block comprises a single piece of material, said block manufactured by sintering of powdered material, by molding, by injection molding, by casting, or combinations thereof.

11. The method of claim 8, wherein the block comprises a plurality of substantially rectangular flat plates arranged in a stack.

12. The method of claim 8, wherein the block comprises two substantially rectangular stepped plates, adapted to mate when stepped plates are coupled together so that the stepped plates form said substantially rectangular block, wherein each stepped plate has at least four steps, and wherein one of two stepped plates has at least one surface slot machined into each step, wherein said two stepped plates when assembled are optionally permanently or temporarily joined by an external bracket, an adhesive, diffusion bonding, an adhesive tape, rivets, fasteners, pins, screws, bolts, or combinations thereof.

13. The method of claim 8, wherein, said steps of moving the device are performed by using a conveyor.

* * * * *